(12) United States Patent
Furukawa

(10) Patent No.: US 11,045,606 B2
(45) Date of Patent: *Jun. 29, 2021

(54) SYRINGE AND PREFILLED SYRINGE

(71) Applicant: TERUMO KABUSHIKI KAISHA, Tokyo (JP)

(72) Inventor: Koichiro Furukawa, Fujinomiya (JP)

(73) Assignee: TERUMO KABUSHIKIKAISHA, Tokyo (JP)

( * ) Notice: Subject to any disclaimer, the term of this patent is extended or adjusted under 35 U.S.C. 154(b) by 167 days.

This patent is subject to a terminal disclaimer.

(21) Appl. No.: 16/362,645

(22) Filed: Mar. 23, 2019

(65) Prior Publication Data

US 2019/0217013 A1 Jul. 18, 2019

Related U.S. Application Data

(63) Continuation of application No. 14/956,102, filed on Dec. 1, 2015, now Pat. No. 10,279,115, which is a
(Continued)

(51) Int. Cl.
*A61M 5/315* (2006.01)
*A61M 5/31* (2006.01)

(52) U.S. Cl.
CPC ...... *A61M 5/31513* (2013.01); *A61M 5/3129* (2013.01); *A61M 5/3134* (2013.01);
(Continued)

(58) Field of Classification Search
CPC .......... A61M 5/31513; A61M 5/31515; A61M 5/31511
See application file for complete search history.

(56) References Cited

U.S. PATENT DOCUMENTS

| 5,413,563 A | 5/1995 | Basile et al. |
| 5,735,825 A | 4/1998 | Stevens et al. |

(Continued)

FOREIGN PATENT DOCUMENTS

| JP | H09-512727 A | 12/1997 |
| JP | 2001-097885 A | 4/2001 |

(Continued)

OTHER PUBLICATIONS

International Search Report dated Aug. 13, 2013 issued in PCT/JP2013/065698.

(Continued)

*Primary Examiner* — Laura A Bouchelle
(74) *Attorney, Agent, or Firm* — Foley & Lardner LLP

(57) ABSTRACT

A syringe includes a gasket, a barrel, and a plunger. The plunger includes a helical rib provided at a head portion, and the gasket includes a threaded engagement portion configured to threaddedly engaged with the helical rib, a plunger-retaining annular rib, and an accommodation portion for accommodating a part of the plunger at which the helical rib is formed. The annular rib includes a rib absent portion for guiding, to the accommodation portion, the helical rib reaching the annular rib. The gasket further includes an intermediate annular rib provided at a part on a proximal side of the retaining annular rib and a part defined on a side of the distal end of the helical projection, between a distal side annular rib and a proximal side annular rib.

16 Claims, 8 Drawing Sheets

Related U.S. Application Data continuation of application No. PCT/JP2013/065698, filed on Jun. 6, 2013.

(52) U.S. Cl.
CPC . *A61M 5/31515* (2013.01); *A61M 2005/3104* (2013.01); *A61M 2005/3131* (2013.01)

(56) References Cited

U.S. PATENT DOCUMENTS

| | | | |
|---|---|---|---|
| 6,129,712 A | 10/2000 | Sudo et al. | |
| 10,279,115 B2 * | 5/2019 | Furukawa | ......... A61M 5/31513 |
| 2012/0184920 A1 | 7/2012 | Okihara et al. | |

FOREIGN PATENT DOCUMENTS

| | | |
|---|---|---|
| JP | 2002-272843 A | 9/2002 |
| JP | 2007-202822 A | 8/2007 |
| JP | 2009-128265 A | 6/2009 |
| JP | 2009-142508 A | 7/2009 |
| JP | 2010-246842 A | 11/2010 |
| WO | WO-01/97885 A1 | 12/2001 |
| WO | WO-2004/075958 A2 | 9/2004 |
| WO | WO-2009/128265 A1 | 10/2009 |

OTHER PUBLICATIONS

Extended European Search Report and Search Opinion issued in European Patent Application No. 13886300.6 dated Nov. 11, 2016.

* cited by examiner

SYRINGE AND PREFILLED SYRINGE

CROSS-REFERENCE TO RELATED PATENT APPLICATIONS

This application is a continuation of U.S. patent application Ser. No. 14/956,102, filed on Dec. 1, 2015, which is a continuation application of and claims the benefit of priority from International Patent Application No. PCT/JP2013/065698, filed Jun. 6, 2013. The contents of these applications are incorporated herein by reference in their entireties.

TECHNICAL FIELD

The present disclosure relates to a syringe, and a syringe prefilled with a liquid medicine.

BACKGROUND

In recent years, prefilled syringes have been frequently used, in which a liquid, such as a liquid medicine, is previously filled. Such prefilled syringes may be filled with a solvent for dissolving a medicine in a vial.

For insertion of a gasket into the prefilled syringe, a method called vacuum capping is generally used. In the method, a barrel comprising a sealed distal end opening is filled with a medicine, the gasket is disposed at an opening portion of the barrel in a reduced-pressure atmosphere (vacuum atmosphere), and then the gasket is inserted into the barrel upon increasing the reduced-pressure atmosphere to a normal pressure state. When a plunger is mounted to the gasket, it is difficult to mount the gasket to the opening portion of the barrel. Accordingly, the capping is performed on the gasket without the plunger. Therefore, in the prefilled syringe, after insertion of the gasket into the barrel, the plunger is generally mounted to the gasket. For easy mounting of the plunger to the gasket, prevention of liquid leakage during mounting the plunger, and inhibition of internal pressure rise, a mounting mechanism has been generally employed in which the plunger is provided with an external threaded portion and the gasket is provided with an internal threaded portion, and the plunger and the gasket are mounted to each other by threaded engagement.

As described above, in the prefilled syringe filled with the solvent, the plunger mounted to the gasket may be operated to be drawn for dissolving the medicine in the vial in the solvent or recovering the dissolved medicine. However, when the plunger is operated to be drawn, there is a risk that the plunger may be separated from the gasket, and the medicine cannot be dissolved or the dissolved medicine cannot be recovered.

There is known a prefilled syringe that comprises, as a mechanism for preventing such separation of the gasket, in an inner cavity portion of the gasket, a plunger retaining annular rib in the back of a helical threaded engagement portion, the helical threaded engagement portion configured for threaded engagement with a helical rib of a plunger. The helical rib of the plunger screwed in the gasket is accommodated in an accommodation portion in the back of the retaining annular rib provided in the inner cavity portion of the gasket, for prevention of separation of the gasket. Such a mechanism for preventing separation is disclosed in JP 2009-142508 A ("Patent Literature 1") proposed by the applicant of the present application. The mechanism comprises a retaining annular rib, but a gasket is prevented from being turned when a plunger is mounted to be screwed therein, and mounting of the plunger to the gasket is facilitated.

A syringe 10 of Patent Literature 1 comprises a gasket 3, a barrel 2, and a plunger 4. The plunger 4 comprises a helical rib 44 provided on an outer surface of a head portion 42, and the gasket comprises a helical threaded engagement portion 33 threadedly engaged with the helical rib 44, a plunger-retaining annular rib 34 positioned on a distal side near the helical threaded engagement portion 33, and an accommodation portion 32 for a part of the head portion 42 of the plunger 4 at which the helical rib is formed. The retaining annular rib 34 comprises a rib absent portion 35 for guiding, to the accommodation portion, the helical rib reaching the retaining annular rib as threaded engagement is advanced between the helical rib of the plunger and the helical threaded engagement portion of the gasket. The syringe 10 is configured so that, when the plunger 4 is mounted to the gasket 3, the helical rib 44 passes the retaining annular rib 34 after passing the rib absent portion 35, and the helical rib 44 does not directly ride over the retaining annular rib 34. Therefore, strong contact between the helical rib 44 and the retaining annular rib 34 is prevented, and the gasket 3 is prevented from being turned due to the turning of the plunger 4 during mounting the plunger 4. Further, the helical rib 44 is not configured to directly ride over the retaining annular rib 34, so that mounting of the plunger 4 is also facilitated.

SUMMARY

In the syringe of Patent Literature 1, the retaining annular rib 34 is provided with the rib absent portion 35, so that the retaining annular rib 34 of the gasket 3 is not brought into strong contact with the helical rib 44 of the plunger 4 upon mounting the plunger 4 to be screwed in the gasket 3. Accordingly, unexpected turning of the gasket 3 caused by turning of the plunger 4 is prevented during mounting, and the mounting of the plunger 4 is facilitated. As a result of an extensive study, the present inventors have found that the retaining annular rib 34 is provided with the rib absent portion 35, so that when the plunger 4 is drawn proximally to be drawn out of the barrel 2 and thereby a force is applied to the retaining annular rib 34, an inner diameter of the retaining annular rib 34 of the gasket 3, made of a soft material such as rubber, is enlarged, and the plunger 4 may be separated from the gasket 3. Therefore, the present inventors have studied a syringe which surely prevents separation of the plunger 4 from the gasket 3 upon application of a force drawing out the plunger 4 from the barrel 2.

It is an object of certain embodiments of the present invention to provide a syringe that is configured to prevent the turning of a gasket upon mounting a plunger, facilitate the mounting of the plunger to the gasket, and surely inhibit the separation of the gasket from the mounted plunger, and a prefilled syringe using the syringe.

A syringe comprises a cylindrically-shaped gasket comprising a closed distal end, an opened proximal end, and an inner cavity portion extending distally from a proximal side. The syringe further comprises a barrel comprising a distal opening portion, the barrel being configured to slidably accommodate the gasket, and a plunger comprising a head portion being configured to be accommodated in the inner cavity portion of the gasket. The plunger comprises a helical rib provided on an outer surface of the head portion. The gasket comprises, on an inner surface of the inner cavity portion, a helical projection forming a threaded engagement portion for threadedly engaging with the helical rib of the plunger, and a plunger retaining annular rib positioned on a distal side near the helical projection. The inner cavity portion further comprises an accommodation portion positioned distally from the retaining annular rib, the accommodation portion accommodating a part of the head portion of the plunger at which the helical rib is formed. The retaining annular rib comprises a rib absent portion for guiding, to the accommodation portion, the helical rib reaching the retaining annular rib as threaded engagement is advanced between the plunger and the gasket. The gasket further comprises, on an outer peripheral surface, a distal side annular rib having an outer diameter larger than an inner diameter of the barrel, a proximal side annular rib having an outer diameter larger than the inner diameter of the barrel, and an intermediate annular rib provided between the distal side annular rib and the proximal side annular rib and provided at a part defined on a side of the retaining annular rib.

DESCRIPTION OF THE EMBODIMENTS

A syringe and a prefilled syringe according to certain embodiments of the present invention will be described below with reference to the drawings.

Figure 1:
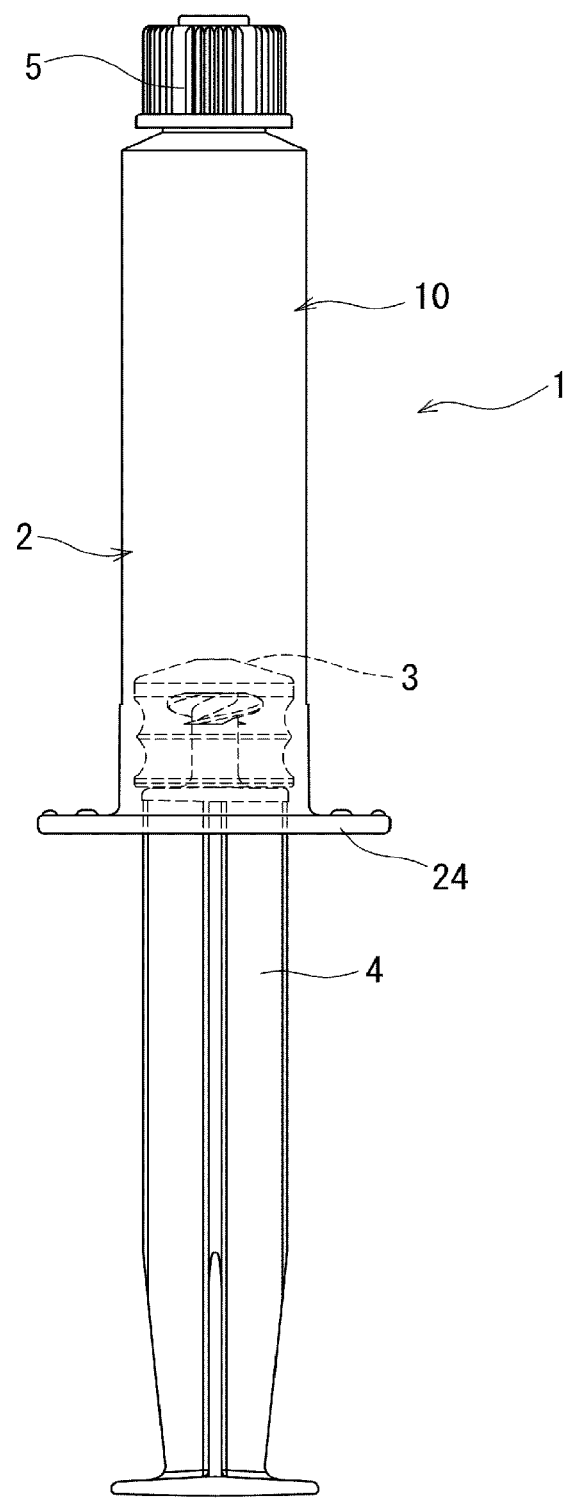
FIG. 1 is a front view of a prefilled syringe having a syringe according to a first embodiment of the present invention.
Figure 2:
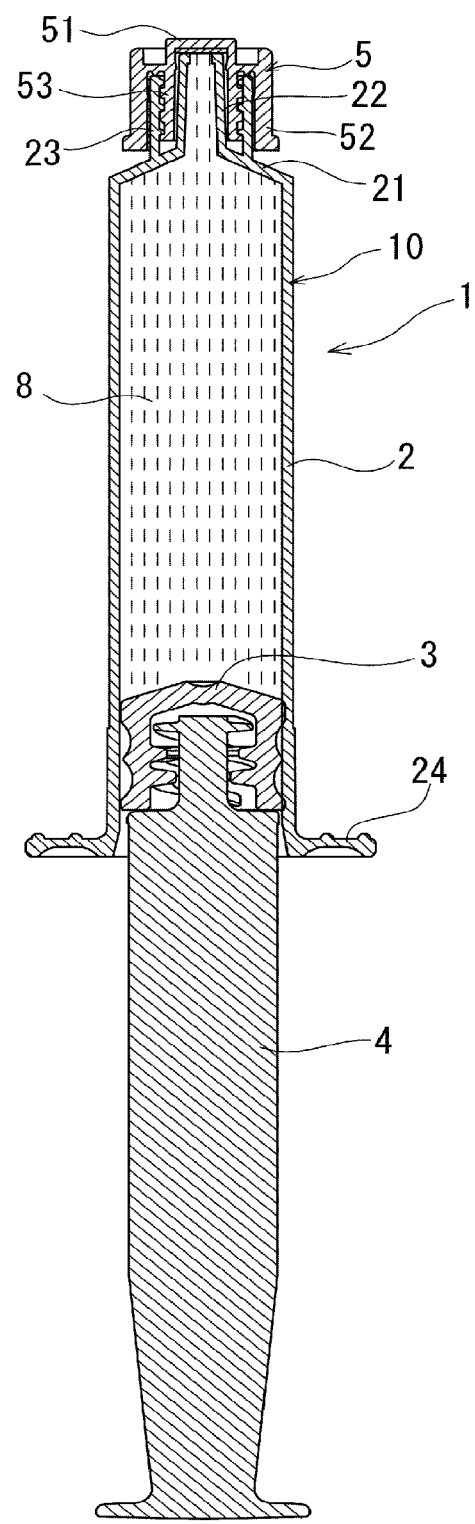
FIG. 2 is a vertical cross-sectional view of the prefilled syringe illustrated in FIG. 1.
Figure 4:
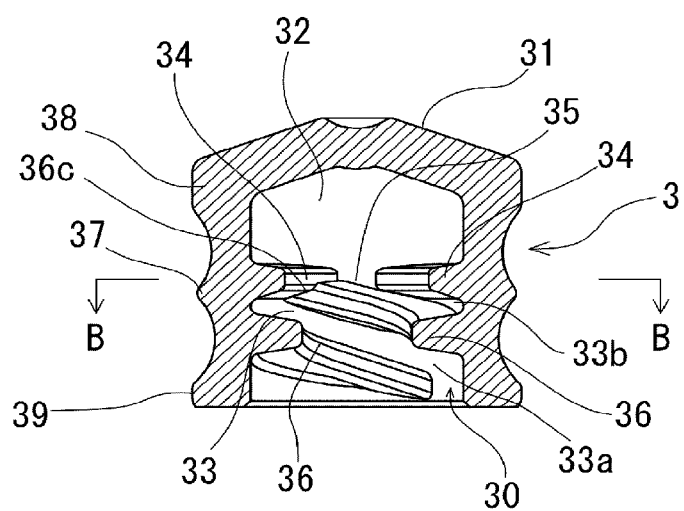
FIG. 4 is a cross-sectional view taken along the line A-A of FIG. 3.
Figure 6:
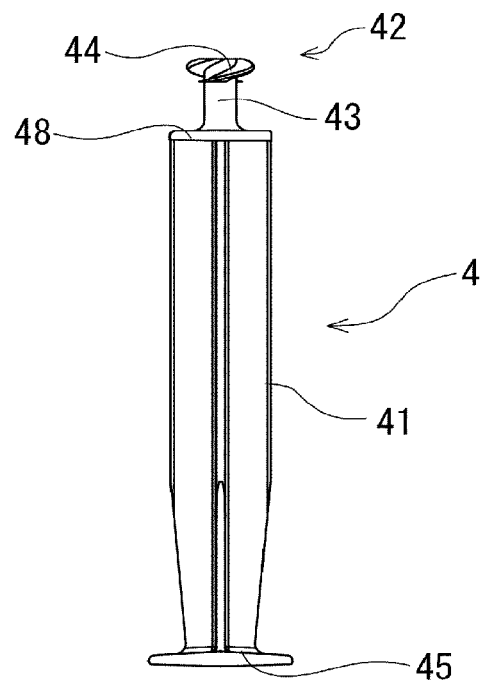
FIG. 6 is a front view of a plunger used for the syringe according to the first embodiment present invention.

As illustrated in FIGS. 1 and 2, a syringe 10 according to an embodiment of the present invention comprises a cylindrically-shaped gasket 3 having a closed distal end, an opened proximal end, and an inner cavity portion 30 extending distally from a proximal side, as illustrated in FIG. 4. The syringe 10 further includes a barrel 2 that comprises a distal opening portion and slidably accommodating the gasket 3, as illustrated in FIG. 2, and a plunger 4 that comprises a head portion 42 accommodated in the inner cavity portion 30 of the gasket 3, as illustrated in FIG. 6.

Figure 8:
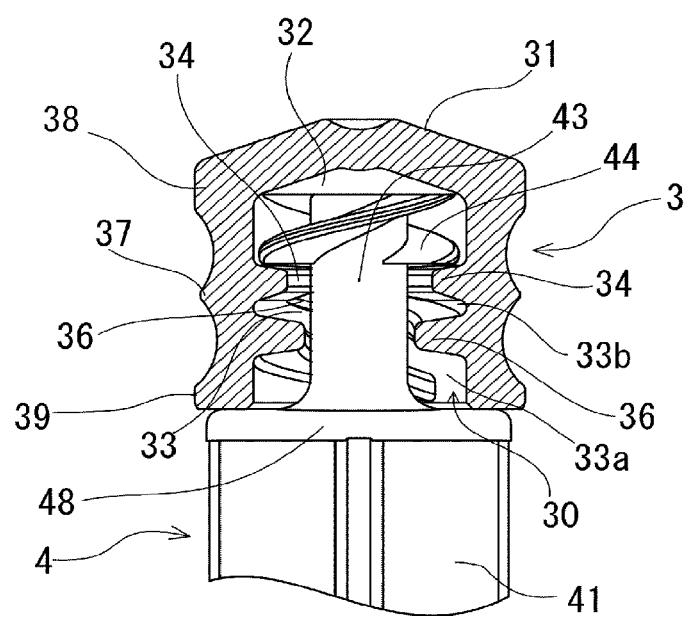
FIG. 8 is a schematic diagram of the gasket of FIGS. 3-5 mounted to the plunger of FIGS. 6-7.

As illustrated in FIG. 8, the gasket 3 comprises, on an inner surface of the inner cavity portion 30, helical projections 36, which form threaded engagement portions that threadedly engage with helical ribs 44 of the plunger 4. The gasket 3 further includes a plunger-retaining annular rib 34 positioned on the distal side near the helical projections 36. Further, the inner cavity portion 30 comprises an accommodation portion 32 positioned distally from the retaining annular rib 34, and accommodating a part of the head portion 42 of the plunger 4 at which the helical ribs 44 are formed. The retaining annular rib 34 comprises rib absent portions 35 for guiding, to the accommodation portion 32, the helical ribs 44 that reach the retaining annular rib 34 as threaded engagement is advanced between the plunger 4 and the gasket 3.

Further, the gasket 3 comprises, on an outer peripheral surface, a distal side annular rib 38 having an outer diameter larger than an inner diameter of the barrel 2, a proximal side annular rib 39 having an outer diameter larger than the inner diameter of the barrel 2, and an intermediate annular rib 37 provided between the distal side annular rib 38 and the proximal side annular rib 39. The intermediate annular rib 37 is provided at a part defined on a side of the retaining annular rib 34.

Accordingly, when the plunger 4 is strongly drawn proximally to expand the retaining annular rib 34 by the helical ribs 44 of the plunger 4, a deformation force applied proximally to the retaining annular rib 34 is transmitted to the intermediate annular rib 37. The intermediate annular rib 37 abuts an inner peripheral surface of the barrel 2 against the transmitted force, and inhibits deformation of the retaining annular rib 34. Therefore, expansion of the retaining annular rib 34 beyond a predetermined extent is prevented. Accordingly, abutment between a proximal end surface of a helical rib 44 and a distal end surface of the retaining annular rib 34 is maintained, and the proximally drawn plunger is prevented from being separated. Further, the retaining annular rib 34 is provided with the rib absent portions 35, so that the helical rib 44 of the plunger 4 can readily ride over the retaining annular rib 34. When the helical rib 44 riding over the retaining annular rib 34 is brought into strong contact with the retaining annular rib 34 near the rib absent portions 35, and thereby resistance is generated, the intermediate annular rib 37 is pressed from the inside and brought into strong contact with an inner surface of the barrel 2. Therefore, the rotational resistance of the gasket 3 is also increased. Accordingly, the intermediate annular rib 37 prevents turning of the gasket 3 when the plunger is mounted, in particular, when the helical rib 44 passes a rib absent portion.

Figure 3:
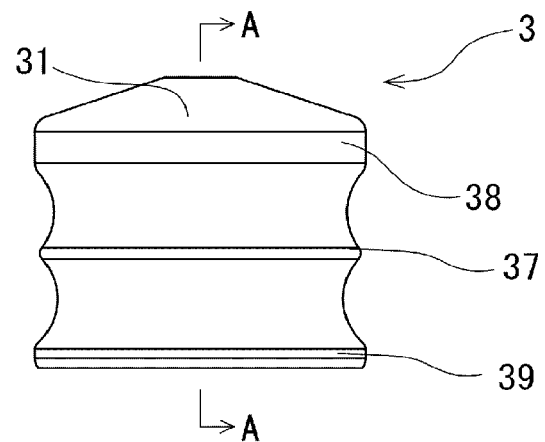
FIG. 3 is an enlarged front view of a gasket used for the syringe according to the first embodiment of the present invention.

Further, as illustrated in FIGS. 1 and 2, the prefilled syringe 1 according to an embodiment of the present invention comprises the syringe 10 for the prefilled syringe, a sealing member 5 for sealing the distal opening portion of the barrel 2, and a medicine 8 stored in the barrel 2. The syringe 10 according to the present example comprises the barrel 2, the gasket 3 slidably accommodated in the barrel 2, and the plunger 4 mounted to or being mountable to the gasket 3. The prefilled syringe 1 comprises the syringe 10, the sealing member 5 for sealing the distal opening portion of the barrel 2, and the medicine 8 stored in the syringe (in the barrel). As illustrated in FIGS. 1 to 5, the gasket 3 according to the present example is a cylindrical body comprising the closed distal end, and the inner cavity portion 30 extending distally from a proximal opening. As illustrated in FIGS. 3 and 4, the gasket 3 comprises, at a distal part, a tapered portion 31 having a diameter reduced in a tapered manner toward a distal side.

The gasket 3 for the syringe comprises the inner cavity portion 30, and the inner cavity portion 30 has a plunger-mounting function. The inner cavity portion 30 comprises, on the inner surface, the helical projections 36 forming the threaded engagement portions 33 for threadedly engaging the helical ribs 44 of the plunger 4, and the plunger-retaining annular rib 34 positioned on the distal side near the helical projections 36. Further, the inner cavity portion 30 comprises the accommodation portion 32 positioned distally from the retaining annular rib 34, and accommodating the part of the head portion 42 of the plunger 4 at which the helical ribs are formed. The retaining annular rib 34 comprises the rib absent portions 35 for guiding, to the accommodation portion 32, the helical ribs 44 reaching the retaining annular rib 34 as threaded engagement is advanced between the helical ribs 44 of the head portion 42 of the plunger 4 and the threaded engagement portions 33 of the gasket 3.

Figure 5:
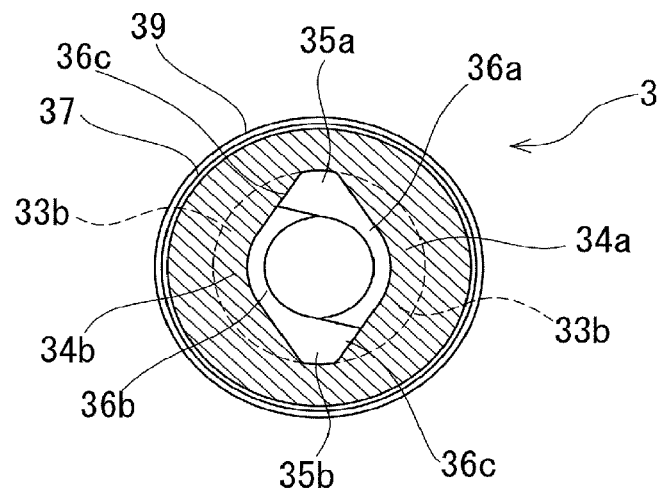
FIG. 5 is a cross-sectional view taken along the line B-B of FIG. 4.

A threaded engagement portion 33 comprises a proximal end 33a near the opening portion of the inner cavity portion 30, distally extends by a predetermined length, and comprises a distal end 33b near the rib absent portion 35 of the retaining annular rib 34. In the present example, the threaded engagement portions 33 are formed to have two threaded engagement portions 33 to correspond to the helical ribs 44 of the head portion 42 of the plunger 4 described below. As illustrated in FIGS. 4 and 5, the gasket 3 according to the present example comprises two helical projections 36 (36a, 36b). Although a plurality of (specifically, two) helical projections as described above is preferably provided, only one helical projection may be provided.

Further, in the present example, the threaded engagement portion 33 is formed as a groove-shaped portion formed between the helical projections 36 projecting from an inner wall surface of the inner cavity portion 30 of the gasket 3. The threaded engagement portion 33 threadedly engages the helical rib 44 of the plunger 4 to distally guide the helical rib 44.

The gasket 3 comprises the plunger-retaining annular rib 34 provided on an inner surface of a part positioned near the threaded engagement portion 33, distally from the threaded engagement portion 33. In the gasket according to the present example, the retaining annular rib 34 is configured to extend in a direction substantially perpendicular to an axis of the gasket 3. The retaining annular rib 34 preferably extends in a direction perpendicular to the axis of the gasket 3, but may be slightly oblique to the perpendicular state. Further, the gasket 3 comprises the accommodation portion 32 positioned distally from the retaining annular rib 34, and accommodates the part of the head portion 42 of the plunger 4 at which the helical ribs are formed.

Further the retaining annular rib 34 comprises the rib absent portion 35 for guiding, to the accommodation portion 32, the helical rib 44 reaching the retaining annular rib 34 as threaded engagement is advanced between the helical rib 44 of the head portion 42 of the plunger 4 and the threaded engagement portion 33 of the gasket 3. In particular, in the gasket 3 according to the present example, the threaded engagement portion 33 is formed as two helical threaded engagement portions corresponding to the two helical ribs, as described above, and the retaining annular rib 34 comprises two rib absent portions provided at substantially opposed positions corresponding to the two threaded engagement portions, as illustrated in FIG. 5. In other words, the gasket 3 comprises two retaining annular ribs 34a and 34b, and the two rib absent portions 35a and 35b positioned between the two retaining annular ribs 34a and 34b. Further, as illustrated in FIG. 5, the retaining annular rib 34 (34a, 34b) preferably comprises a rib gradually reduced in size toward the rib absent portion 35 (35a, 35b). It is noted that the retaining annular rib 34 (34a, 34b) may have a width gradually reduced, a height gradually reduced, or a width gradually reduced and a height gradually reduced, toward the rib absent portion 35 (35a, 35b). As the retaining annular rib 34 is configured as described above, passage of the helical rib 44 of the plunger 4 through the retaining annular rib 34, i.e., entrance of the helical rib 44 of the plunger 4 into the accommodation portion 32, is further facilitated. It is noted that in the rib absent portion, even if the retaining annular rib is not completely absent, the retaining annular rib is preferably partially absent to have a function for guiding the helical rib of the head portion.

Each helical projection 36 comprises a proximal end near the opening portion of the inner cavity portion 30, distally extends by a predetermined length, and comprises a distal end 36c connected to a part adjacent to the rib absent portion 35 of the retaining annular rib 34. The helical projection 36 comprises a surface on the distal side of a distal end part, positioned adjacent to a proximal end of the rib absent portion 35. Therefore, the helical rib 44 can pass through the rib absent portion 35 without considerably deforming the retaining annular rib 34 near the rib absent portion 35 to ride over the retaining annular rib 34. Although the retaining annular rib 34 is difficult to deform owing to the intermediate annular rib 37, the rib absent portion 35 allows the helical rib 44 to ride over the retaining annular rib 34 without considerably deforming the retaining annular rib 34. Therefore, the mounting of the plunger 4 to the gasket 3 is facilitated. Further, in the present example, the retaining annular rib 34 comprises one end and the other end formed by the absent portion 35. The distal end part of the helical projection 36 is positioned close to the absent portion 35 and distally extends obliquely, and the distal end part of the helical projection 36 comprises a distal end connected to a proximal side surface of one end of the retaining annular rib 34.

As illustrated in FIG. 4, a distance between the helical projection 36 and the retaining annular rib 34 is configured to be reduced toward the rib absent portion 35 (similarly, toward the distal end 33b of the threaded engagement portion 33). Therefore, the helical rib 44 of the plunger 4 is surely guided to the rib absent portion 35 of the retaining annular rib 34. Further, the helical projection 36 for forming the threaded engagement portion 33 of the gasket 3 preferably has a projection height higher than a projection height of the retaining annular rib 34. This is because threaded engagement between the helical projection 36 and the helical rib 44 is readily and surely maintained in order to surely pass the helical rib 44 of the plunger 4 to be turned through the rib absent portion 35 of the retaining annular rib 34 to accommodate the part at which the helical ribs 44 are formed in the accommodation portion 32 upon mounting the plunger 4 to the gasket 3.

Although the height (inward projection length) of the retaining annular rib 34 is different depending on the size or hardness of the gasket, the height is preferably 0.5 to 2.0 mm, in particular, 0.8 to 1.5 mm. Further, the width of the rib absent portion 35 of the retaining annular rib 34 in a circumferential direction of the gasket 3 is preferably 0.5 to 3.0 mm, in particular, 0.5 to 1.5 mm.

Further, the gasket 3 comprises a small projection portion projecting toward the proximal side, at a center part of an inner surface of a distal end part. The projection portion is configured to abut on a distal end of the head portion of the plunger upon proximal deformation of the distal end part of the gasket 3, and excessive deformation of the distal end part of the gasket 3 is prevented. The projection portion preferably has a substantially semi-spherical shape. The gasket 3 generally has a diameter of 5 to 30 mm, and a total length of approximately 5 to 30 mm.

The gasket 3 comprises, on the outer peripheral surface, the distal side annular rib 38 having an outer diameter larger than the inner diameter of the barrel 2, the proximal side annular rib 39 having an outer diameter larger than the inner diameter of the barrel 2, and the intermediate annular rib 37 provided between the distal side annular rib 38 and the proximal side annular rib 39.

The distal side annular rib 38 is provided on an outer surface of a distal end part of a cylindrical main body portion, and the proximal side annular rib 39 is provided on an outer surface of a proximal end part of the main body portion. The distal side annular rib 38 and the proximal side annular rib 39 preferably have an outer diameter larger than the inner diameter of the barrel 2 by 0.5 to 1.5 mm, and in particular, when the inner diameter of the barrel 2 is 8 to 10 mm, the outer diameters of the annular ribs are preferably larger than the inner diameter of the barrel 2 by 0.5 to 0.8 mm. Therefore, while maintaining liquid tightness between the gasket 3 and the inner peripheral surface of the barrel 2, sliding resistance of the gasket 3 sliding in the barrel 2 can be reduced. Further, the distal side annular rib 38 and the proximal side annular rib 39 each have an outermost projecting top part extending linearly in the axial direction of the gasket 3. The top part of the distal side annular rib 38 is preferably formed to have a large width in the axial direction, as illustrated in FIG. 3. The top part of the distal side annular rib 38 preferably has an axial length longer than an axial length of the proximal side annular rib 39. The axial length of the distal side annular rib 38 is preferably 0.8 to 2 mm, in particular, 0.8 to 1.5 mm. The axial length of the proximal side annular rib 39 is preferably 0.1 to 1.0 mm, in particular, 0.2 to 0.5 mm. Owing to the configuration as described above, a contact area between the gasket 3 and the inner peripheral surface of the barrel 2 is increased, and the liquid tightness is increased and the liquid medicine is not likely to leak.

The intermediate annular rib 37 is provided on the outer peripheral surface of the gasket 3, and is formed between the distal side annular rib 38 and the proximal side annular rib 39. The intermediate annular rib 37 is circumferentially provided along the outer peripheral surface of the gasket 3, in a direction perpendicular to the axis of the gasket 3. Further, as illustrated in FIGS. 3 to 5, the intermediate annular rib 37 is formed over the whole periphery of the gasket 3 to uniformly project from the outer peripheral surface of the gasket 3.

As illustrated in FIG. 4, the intermediate annular rib 37 is provided at the part defined on a side of the retaining annular rib. Further, when the plunger 4 is strongly drawn proximally, the deformation force applied proximally to the retaining annular rib 34 is transmitted to the outer peripheral surface of the gasket 3 positioned slightly proximally from the distal end surface of the retaining annular rib 34. Therefore, the intermediate annular rib 37 is preferably positioned proximally from the distal end surface of the retaining annular rib 34. Therefore, deformation of the retaining annular rib 34 is surely prevented, abutment between the proximal end surface of the helical rib 44 and the distal end surface of the retaining annular rib 34 is surely maintained, and separation of the plunger 4 from the gasket 3 is surely prevented.

It is noted that, in the present example, the intermediate annular rib 37 is provided to have an outermost projecting top part positioned at a side part on a proximal side of the retaining annular rib 34. Further, the intermediate annular rib 37 is provided at a part on the proximal side of the retaining annular rib 34, and a part defined on a side of the distal end 36c of the helical projection 36. Specifically, the intermediate annular rib is configured to have the outermost projecting top part positioned slightly proximally from an innermost projecting top part of the retaining annular rib 34. It is noted that the intermediate annular rib 37 has at least a part distal from the top part, and the part is axially superposed on a part on the proximal side of the retaining annular rib 34.

Further, as illustrated in FIG. 4, the intermediate annular rib 37 is formed to axially overlap the distal end 36c of the helical projection 36. Additionally, as illustrated in FIG. 4, in the gasket 3 according to the present example, the distal end 36c of the helical projection 36 is connected to the part adjacent to the rib absent portion 35 of the retaining annular rib 34. The intermediate annular rib 37 is disposed so that the top part thereof is positioned near a connected part (distal end 36c). In the gasket 3 according to the present example, the retaining annular rib 34 is perpendicular to the axis of the gasket 3, and correspondingly the intermediate annular rib 37 is similarly configured.

As illustrated in FIG. 4, the intermediate annular rib 37 has an outer diameter smaller than the outer diameter of the distal side annular rib 38 and the outer diameter of the proximal side annular rib 39. Therefore, the sliding resistance of the gasket 3 sliding in the barrel 2 can be reduced. Further, the outer diameter of the intermediate annular rib 37 is larger than the inner diameter of the barrel 2. Accordingly, when the plunger 4 is strongly drawn proximally, the intermediate annular rib 37 surely abuts on the inner peripheral surface of the barrel 2, and deformation of the retaining annular rib 34 can be surely inhibited.

Further, the contact area between the intermediate annular rib 37 and the inner peripheral surface of the barrel 2 is preferably reduced relative to a contact area between the distal side annular rib 38 and the inner peripheral surface of the barrel 2 and a contact area between the proximal side annular rib 39 and the inner peripheral surface of the barrel 2. As configured as described above, contact resistance (sliding resistance) of the gasket 3 against the barrel 2 can be reduced upon vacuum capping of the gasket 3 to the barrel 2 or upon operation of the plunger 4, and liquid tightness of the medicine 8 to be filled is secured by the distal side annular rib 38 and the proximal side annular rib 39.

Further, in the present example, the intermediate annular rib 37 has a vertical cross-section comprising a top part transversely projecting to form a chevron shape, and a distal end of the top part can abut on the inner surface of the barrel 2. The cross-section is formed into the chevron shape comprising the top part, and a contact area between the intermediate annular rib 37 and the inner peripheral surface of the barrel 2 can be reduced. For further restriction of deformation of the retaining annular rib 34, an area of an abutment part of the intermediate annular rib making contact with the inner peripheral surface of the barrel 2 may be increased to sufficiently support the intermediate annular rib. In this configuration, the intermediate annular rib is preferably configured to have the vertical cross-section having, for example, a rectangular shape or a semi-spherical shape.

The outer diameter of the intermediate annular rib is preferably larger than the inner diameter of the barrel 2 by 0 to 1.0 mm, and in particular, when the inner diameter of the barrel 2 is 8 to 10 mm, the outer diameter of the intermediate annular rib is preferably larger than the inner diameter of the barrel 2 by 0.1 to 0.5 mm. Therefore, while inhibiting the deformation of the retaining annular rib 34 upon proximally drawing the plunger 4, the sliding resistance of the gasket 3 sliding in the barrel 2 can be reduced. It is noted that as long as the deformation of the retaining annular rib 34 is inhibited by abutment of the intermediate annular rib 37 on the inner peripheral surface of the barrel 2, upon proximally drawing the plunger 4 strongly, the outer diameter of the intermediate annular rib may be reduced relative to the inner diameter of the barrel 2.

As a component material of the gasket 3, a known material conventionally used for gaskets can be employed. The material includes, for example, a rubber, an elastomer, a polyolefin-based resin, a fluorine-based resin, or a polyester-based resin. The rubber preferably includes, for example, a natural rubber, an isoprene rubber, a butyl rubber, a chloroprene rubber, a nitrile-butadiene rubber, a styrene-butadiene rubber, or a silicone rubber, especially a vulcanized rubber. The elastomer preferably includes, for example, a polyvinyl chloride-based elastomer, a polyolefin-based elastomer, a styrene-based elastomer, a polyester-based elastomer, a polyamide-based elastomer, a polyurethane-based elastomer, or a mixture thereof. The styrene-butadiene rubber, the butyl rubber, or the styrene-based elastomer is preferably selected from the above-mentioned rubbers and elastomers. The styrene-butadiene rubber, butyl rubber, and styrene-based elastomer have a preferred hardness and elastic property, and can be adapted for a sterilization method, such as γ-sterilization, electron-beam sterilization, or high-pressure steam sterilization.

Further, a part on the distal side of the gasket may be coated with a low medicine-adsorbing material or the like. As a material of a low medicine-adsorbing layer, a known material conventionally used for laminate gaskets can be used. The material of the low medicine-adsorbing layer includes, for example, a polyolefin-based resin, a fluorine-based resin, or a polyester-based resin. Specifically, the polyolefin-based resin preferably includes a polypropylene, an ultrahigh molecular weight polyethylene, a poly(4-methylpentene-1), a cyclic polyolefin, or the like. The fluorine-based resin preferably includes a tetrafluoroethylene-perfluoroethoxyethylene copolymer, a polytetrafluoroethylene, a tetrafluoroethylene/perfluoro(alkyl vinyl ether) copolymer, a tetrafluoroethylene/hexafluoropropylene copolymer, or the like. Further an outer surface of the gasket 3, or at least surfaces of the distal side annular rib 38, the proximal side annular rib 39, and the intermediate annular rib 37 are preferably coated with a lubricant agent. As the lubricant agent, a silicone oil is preferably employed.

Figure 9:
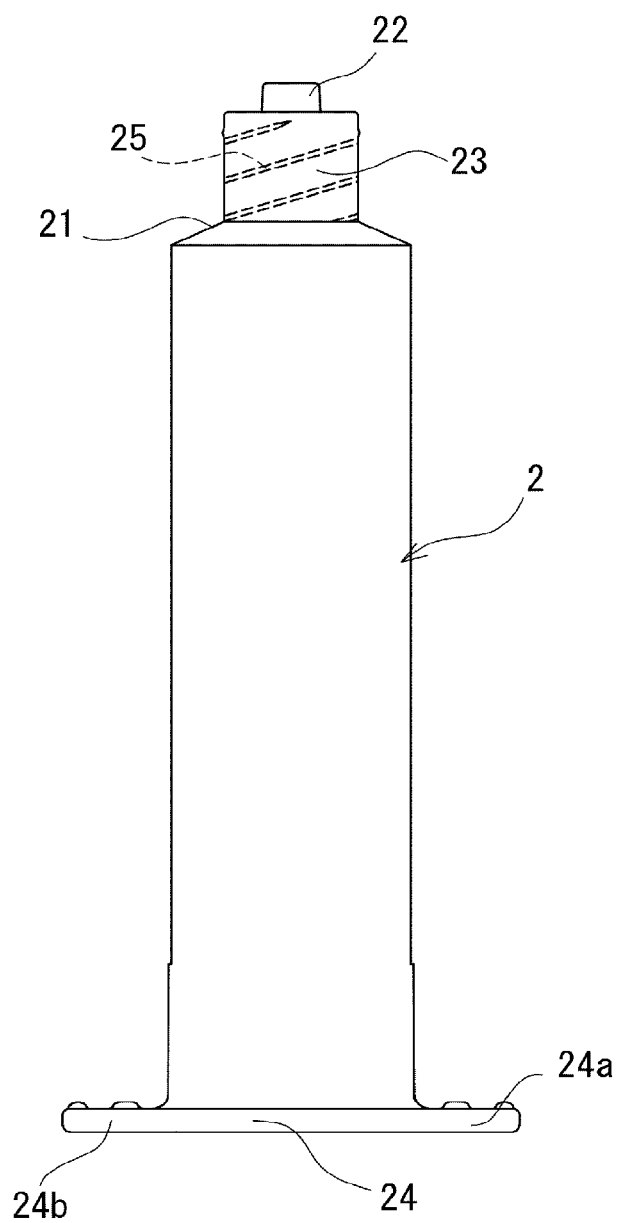
FIG. 9 is a partially cutaway front view of one example of a barrel used for the syringe according to the first embodiment of the present invention.

As illustrated in FIG. 1, FIG. 2, and FIGS. 6 to 8, the plunger 4 comprises a plunger body portion 41, and the head portion 42 projecting distally from the plunger body portion 41. The plunger body portion 41 comprises a disk portion 48 positioned at a distal end and comprising the head portion 42 projecting therefrom, and a pressing portion 45 positioned at a proximal end. As illustrated in FIGS. 6 and 9, the plunger body portion 41 comprises a shaft portion having a cross-shaped cross-section, and the shaft portion is provided, at a distal end, with the disk portion 48, and is provided, at a proximal end, with the pressing portion 45 for the plunger, having a disk-shape.

Figure 7:
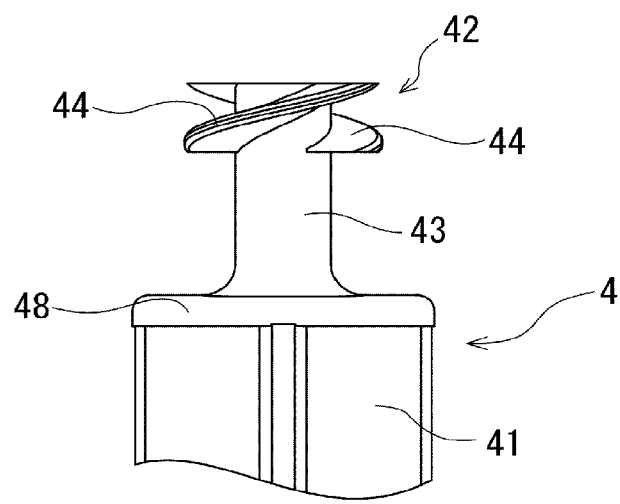
FIG. 7 is an enlarged right side view of a distal end part of the plunger illustrated in FIG. 6.

The head portion 42 is a projection portion provided at a distal end part of the plunger 4. The head portion 42 projects forward from near the center of the disk portion 48 provided at the distal end of the body portion 41. The head portion 42 is configured to have a rod shape. As illustrated in FIGS. 6 to 8, the head portion 42 comprises a shaft portion 43, and the helical rib 44 formed on an outer surface of the shaft portion 43. Further, the shaft portion 43 comprises a flat distal end. The shaft portion 43 may have a cylindrical shape or a columnar shape, and may have a cross-section of a polygonal shape, such as a square, pentagonal, hexagonal, or cruciform shape.

The helical rib 44 is formed on an outer surface of a distal end of the head portion 42 of the plunger 4, in particular, on an outer surface of a distal end of the shaft portion 43. As illustrated in FIGS. 6 to 8, in the plunger 4 according to the present example, two helical ribs 44 are formed corresponding to the above-mentioned threaded engagement portions 33 of the gasket 3. The helical rib 44 is configured to have a starting end at the distal end part of the head portion 42 of the plunger 4, specifically at the distal end of the shaft portion 43, and proximally extends by a predetermined length. Although a plurality of (specifically, two) helical ribs as described above is preferably provided, only one helical rib may be provided.

The helical rib 44 of the plunger 4 preferably has a height (outward projection length) as described below. The helical rib 44 of the plunger 4 preferably has a height of 0.5 to 2.5 mm, in particular, 1.0 to 2.0 mm. As a component material of the plunger 4, a hard or semi-hard resin, such as a high-density polyethylene, a polypropylene, a polystyrene, a polyethylene terephthalate, is preferably used.

The barrel 2 comprises a cylindrical body including a transparent or translucent material, preferably a material having reduced oxygen permeability or water vapor permeability. As illustrated in FIGS. 2 and 9, the barrel 2 comprises a nozzle portion 22 and a collar 23. The nozzle portion 22 is provided at a distal end of the barrel 2, comprises a distal opening portion for ejecting the liquid medicine or the like in the barrel, and is formed to have a diameter distally reduced into a tapered shape. The collar 23 is formed concentrically with the nozzle portion 22 into a cylindrical shape to surround the nozzle portion 22. Further, the collar 23 has an opening distal end, and the collar 23 has an inner diameter and an outer diameter each substantially constant from a proximal end (barrel distal end surface 21) to the distal end. Further, the nozzle portion 22 comprises a distal end part projecting from the opening distal end of the collar 23, and the distal end parts of the nozzle portion 22 and the collar 23 are chamfered to facilitate the accommodation of the nozzle portion 22 and the collar 23 in the sealing member (sealing cap) 5.

The collar 23 comprises an inner peripheral surface in which a thread groove (threaded engagement portion on the barrel side) 25 is formed for threaded engagement with a thread (threaded engagement portion on the cap side) 54 formed on a below-mentioned nozzle accommodation portion 53 of the sealing cap 5. Therefore, the barrel 2 and the sealing cap 5 are threadedly engaged between the inner peripheral surface of the collar 23 and an outer peripheral surface of the nozzle accommodation portion 53. Further, the thread groove (threaded engagement portion on the barrel side) 25 serves as a portion for mounting an injection needle (hub for the injection needle), after the sealing cap 5 is removed from the barrel. As illustrated in FIGS. 1, 2, and 9, the barrel 2 comprises a flange 24. The flange 24 is a disk portion having an elliptical torus shape formed to project perpendicularly from the whole circumference of a proximal end of the barrel 2. As illustrated in FIGS. 1, 2, and 9, the flange 24 comprises two opposed grip portions 24a and 24b having a wide width, and the grip portion comprises a distal side on which a plurality of ribs is formed.

Figure 10:
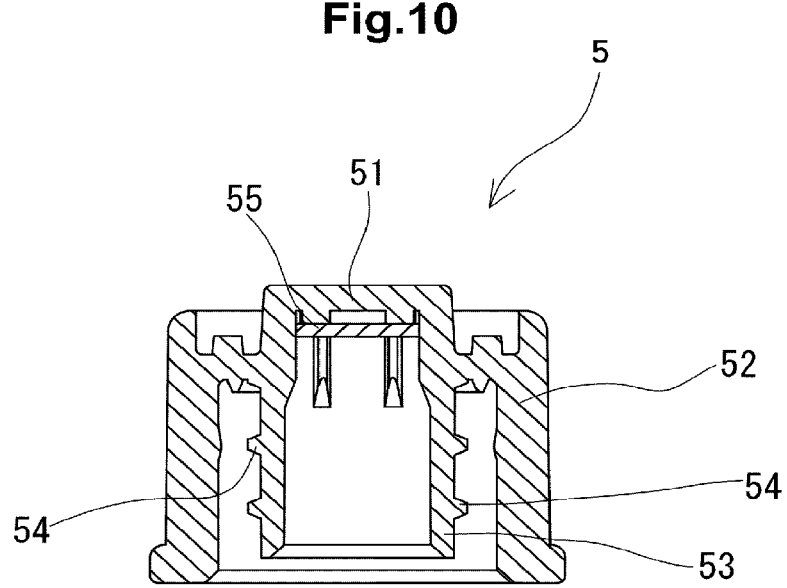
FIG. 10 is a cross-sectional view of one example of a sealing cap used for the syringe according to the first embodiment of the present invention.

A material of the barrel 2 includes, for example, a resin, such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester, such as a polyethylene terephthalate, or a cyclic polyolefin. In particular, a resin such as a polypropylene or a cyclic polyolefin is preferably employed for easy moldability and heat resistance. As illustrated in FIGS. 1, 2, and 10, the sealing cap 5 as the sealing member comprises a closed end 51, the nozzle accommodation portion 53, and a collar accommodation portion 52.

The nozzle accommodation portion 53 is provided at a center part of the sealing cap 5, comprises a closed distal end, and is formed into a cylindrical shape. The nozzle accommodation portion 53 has an inner diameter formed slightly larger than that of the nozzle portion 22, the inner diameter is configured to be slightly increased toward the proximal end from the distal end into a tapered shape, and accommodate the whole nozzle portion 22 from a proximal opening. The nozzle accommodation portion 53 comprises an inside closed surface (inner surface of the closed end 51) on which a sealing member 55 for liquid-tightly sealing the distal opening portion of the barrel 2 is accommodated. The sealing member 55 preferably includes an elastic member for liquid-tightly sealing the distal opening portion of the barrel 2. A material of the sealing member preferably includes, for example, natural rubber, a synthetic rubber, such as an isoprene rubber, a butadiene rubber, a fluororubber, a silicone rubber, or a thermoplastic elastomer, such as an olefinic elastomer or a styrene elastomer. Further, the nozzle accommodation portion 53 comprises an outer surface on which the thread (threaded engagement portion on the cap side) 54 is formed for threaded engagement with the thread groove (threaded engagement portion on the barrel side) 25 formed on an inner surface of the collar 23 of the barrel 2. Therefore, the barrel 2 and the sealing cap 5 are threadedly engaged with each other between the outer surface of the nozzle accommodation portion 53 and the inner surface of the collar 23.

The collar accommodation portion 52 comprises a cylindrical body formed to surround the nozzle accommodation portion 53 and comprising a closed distal end, and accommodates the collar 23 between an inner surface of the collar accommodation portion 52 and the outer surface of the nozzle accommodation portion 53. Further, the collar accommodation portion 52 formed into a cylindrical shape is concentric with the nozzle accommodation portion 53, and the collar accommodation portion 52 has an inner diameter having a substantially constant diameter from the distal end to the proximal end. Further, as illustrated in FIG. 1, the sealing cap 5 comprises an outside surface (outer peripheral surface of the collar accommodation portion 52) which is vertically knurled to prevent slip of fingers or the like upon turning the sealing cap 5. A material of the sealing cap 5 includes for example a resin, such as a polypropylene, a polyethylene, a polystyrene, a polyamide, a polycarbonate, a polyvinyl chloride, poly(4-methyl pentene-1), an acrylic resin, an acrylonitrile-butadiene-styrene copolymer, a polyester such as polyethylene terephthalate, or a cyclic polyolefin. In particular, a resin such as a polypropylene or a cyclic polyolefin is preferably employed for easy moldability and heat resistance.

As illustrated in FIGS. 1 and 2, the prefilled syringe 1 according to an embodiment of the present invention comprises the above-mentioned syringe 10, the sealing member 5 for sealing the distal opening portion of the barrel 2, and the medicine 8 filled in a space formed by the gasket 3. The medicine 8 may include any medicine, for example, a liquid medicine, such as a cyclosporine, a benzodiazepine, a sodium chloride injection solution, a vitamin preparation, or a mineral, a solvent, such as a physiological saline solution, or a powdered or freeze-dried medicine or a liquid medicine such as an antibiotic or a protein preparation. The prefilled syringe according to an embodiment of the present invention is particularly suitable for a prefilled syringe filled with a solvent for dissolving a medicine stored in a vial. Such a solvent includes a physiological saline solution, injection water, a glucose solution, or the like.

Next, an effect between the syringe 10 and the prefilled syringe 1 according to an embodiment of the present invention will be described using FIGS. 7 and 8. The prefilled syringe 1 according to the present example is provided, for example, in a state in which the gasket 3 and the plunger 4 are separated from each other. The plunger 4 is mounted to the gasket 3 when used.

Then, after the helical rib 44 of the plunger 4 is inserted into the proximal end of the threaded engagement portion 33 of the gasket 3, the plunger 4 is turned to advance the threaded engagement between the helical rib 44 and the threaded engagement portion 33. When the plunger 4 is further turned, the helical rib 44 passes through the rib absent portion 35 of the retaining annular rib 34 to enter the accommodation portion 32. When the plunger keeps turning, the whole of the helical rib 44 passes through the rib absent portion 35 of the retaining annular rib 34, and the part of the head portion 42 of the plunger 4 at which the helical ribs are formed is configured to be accommodated in the accommodation portion 32 of the gasket 3, as illustrated in FIG. 8. Thus, mounting of the plunger 4 to the gasket 3 is completed. In the mounting operation, the helical rib 44 passes the annular rib after passing the rib absent portion 35, and the helical rib 44 does not directly ride over the retaining annular rib 34. Therefore, strong contact between the helical rib 44 and the retaining annular rib 34 is prevented, and the gasket is prevented from being turned due to the turning of the plunger during the mounting operation.

While the plunger 4 is mounted to the gasket 3, the proximal end surface of the helical rib 44 of the plunger 4 abuts a distal end surface of the retaining annular rib 34 of the gasket 3, and the separation of the plunger 4 from the gasket 3 is restricted. Further, the plunger 4 is configured to slip while the part of the head portion 42 of the plunger 4 at which the helical ribs are formed is accommodated in the accommodation portion 32 of the gasket 3. Further, even if the plunger 4 turns in any direction in a normal state, the proximal end of the helical rib 44 does not enter the rib absent portion 35 of the retaining annular rib 34, and the separation of the plunger 4 and turning of the gasket 3 caused by the turning of the plunger 4 is inhibited.

As described above, the proximal end surface of the helical rib 44 of the plunger 4 abuts the distal end surface of the retaining annular rib 34 of the gasket 3, and the separation of the plunger 4 from the gasket 3 is restricted. Further, when the plunger 4 is drawn proximally, the helical rib 44 expands the retaining annular rib 34, and the intermediate annular rib 37 abuts on the inner peripheral surface of the barrel 2 to restrict expansion of the retaining annular rib 34 beyond the predetermined extent. In particular, the retaining annular rib 34 is provided with the rib absent portion 35 so that the helical rib 44 easily rides over the retaining annular rib 34. However, the proximal end surface of the helical rib 44 maintains abutment with the distal end surface of the retaining annular rib 34, so that the intermediate annular rib 37 resists drawing out of the plunger 4, and the plunger 4 is prevented from being separated. It is noted that since the intermediate annular rib 37 can also restrict the expansion of the vicinity of the distal end of the helical projection 36, even if the helical rib 44 is drawn out of the retaining annular rib 34, the abutment between the helical projection 36 and the helical rib 44 also can be maintained to prevent immediate separation of the plunger 4.

Figure 11:
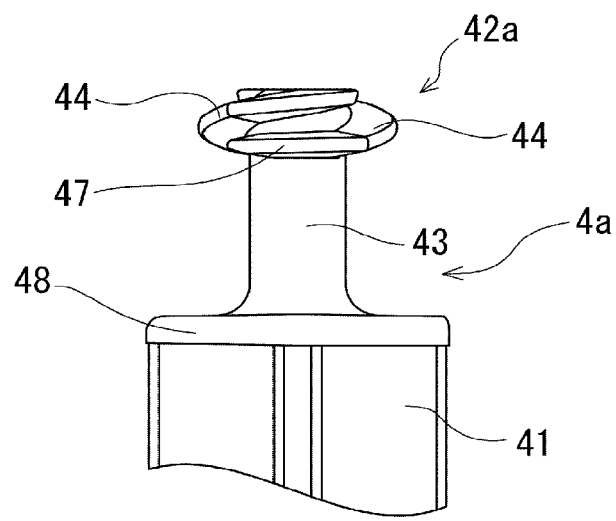
FIG. 11 is an enlarged front view of a distal end part of a plunger according to another example.
Figure 12:
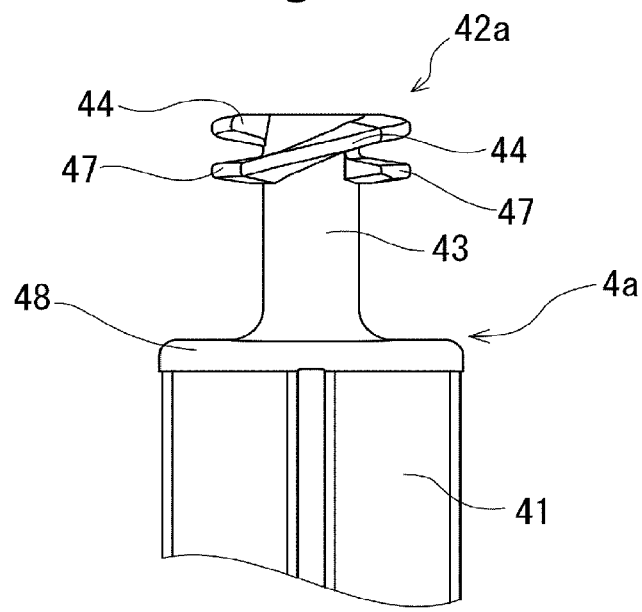
FIG. 12 is a right side view of the plunger illustrated in FIG. 11.
Figure 13:
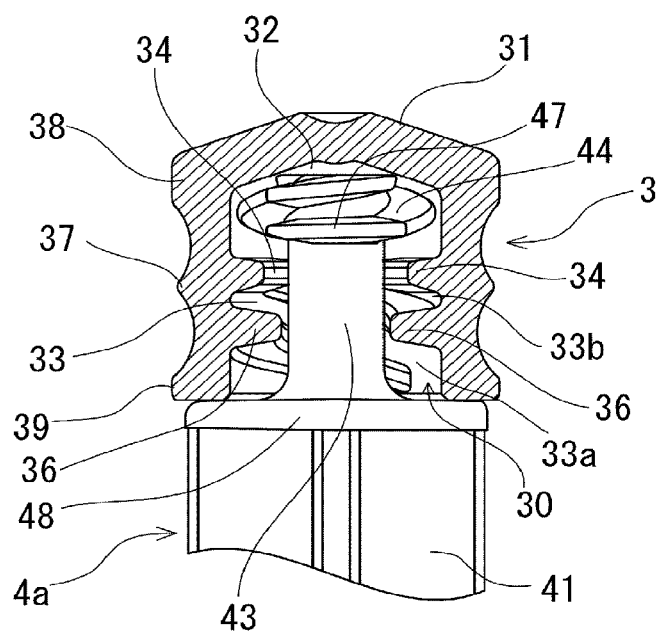
FIG. 13 is a schematic diagram illustrating an effect upon mounting a gasket to the plunger illustrated in FIGS. 11 and 12.

It is noted that a plunger used for the syringe 10 according to an embodiment of the present invention may be a plunger 4a having a distal end shaped as illustrated in FIGS. 11 to 13.

The plunger 4a is different from the above-mentioned plunger 4 only in the form of the helical rib.

The helical rib 44 is formed on an outer surface of a distal end of a head portion 42a of the plunger 4a, in particular, on the outer surface of the distal end of the shaft portion 43. Further, also in the plunger 4a according to the present example, as illustrated in FIGS. 11 to 13, two helical ribs 44 are formed corresponding to the above-mentioned threaded engagement portions 33 of the gasket 3. The helical rib 44 is configured to have the starting end at the distal end part of the head portion 42a of the plunger 4a, specifically, at the distal end of the shaft portion 43, and proximally extend by a predetermined length. Although the plurality of (specifically, two) helical ribs as described above is preferably provided, only one helical rib may be provided.

In the plunger 4a according to the present example, the helical rib 44 comprises a circumferentially extending portion 47 extending in a circumferential direction of the shaft portion 43 at the proximal end of the helical rib 44. The circumferentially extending portion 47 extends by a predetermined length in the circumferential direction, substantially perpendicular to the axis of the shaft portion 43. Therefore, the circumferentially extending portion 47 substantially does not have a helical form. The circumferentially extending portion 47 comprises a substantially flat proximal end surface. Further, the circumferentially extending portion 47 is configured to pass through the threaded engagement portion 33 of the gasket 3 and the rib absent portion of the retaining annular rib 34. A center angle of the circumferentially extending portion 47 is preferably 30 to 150 degrees, in particular, 80 to 100 degrees. It is noted that, here, the center angle of the circumferentially extending portion represents an angle between two lines connecting the axis of the shaft portion and a starting end and a terminal end of the circumferentially extending portion, respectively.

Similarly to the above-mentioned plunger 4, in the gasket 3, the plunger 4a is configured so that after the helical rib 44 of the plunger 4a is inserted into the proximal end of the threaded engagement portion 33 of the gasket 3, the plunger 4a is turned to advance the threaded engagement between the helical rib 44 and the threaded engagement portion 33. When the plunger 4a is further turned, the helical rib 44 passes through the rib absent portion 35 of the retaining annular rib 34 to enter the accommodation portion 32. When the plunger keeps turning, the whole of the helical rib 44 passes through the rib absent portion 35 of the retaining annular rib 34, and the part of the head portion 42a of the plunger 4a at which the helical ribs are formed is accommodated in the accommodation portion 32 of the gasket 3, as illustrated in FIG. 13.

While the plunger 4a is mounted to the gasket 3, the proximal end surface of the helical rib 44 (circumferentially extending portion 47) of the plunger 4a abuts on the distal end surface of the retaining annular rib 34 of the gasket 3, and the separation of the plunger 4a from the gasket 3 is restricted. Further, in the plunger 4a according to the present example, the helical rib 44 comprises the circumferentially extending portion 47 at the proximal end. The proximal end surface of the circumferentially extending portion 47 is larger in size than the proximal end surface of the helical rib 44 of the plunger 4 illustrated in FIG. 7. Therefore, the proximal end surface of the helical rib 44 of the plunger 4a abutting on the distal end surface of the retaining annular rib 34 is increased in size, and separation of the plunger 4a from the gasket 3 is surely prevented when the plunger 4a is drawn proximally.

The syringe according to certain embodiments of the present invention comprises the following.

(1) A syringe comprises a cylindrically-shaped gasket comprising a closed distal end, an opened proximal end, and an inner cavity portion extending distally from a proximal side. The syringe further comprises a barrel comprising a distal opening portion, the barrel being configured to slidably accommodate the gasket, and a plunger comprising a head portion being configured to be accommodated in the inner cavity portion of the gasket. The plunger comprises a helical rib provided on an outer surface of the head portion, and the gasket comprises, on an inner surface of the inner cavity portion, a helical projection being configured to threadedly engage with the helical rib of the plunger and a plunger retaining annular rib positioned on a distal side near the helical projection. The inner cavity portion further comprises an accommodation portion positioned distally from the retaining annular rib, the accommodation portion being configured to accommodate a part of the head portion of the plunger at which the helical rib is formed. The retaining annular rib comprises a rib absent portion for guiding, to the accommodation portion, the helical rib reaching the retaining annular rib as threaded engagement is advanced between the plunger and the gasket. The gasket further comprises an outer peripheral surface comprising a distal side annular rib having an outer diameter larger than an inner diameter of the barrel, a proximal side annular rib having an outer diameter larger than the inner diameter of the barrel, and an intermediate annular rib provided between the distal side annular rib and the proximal side annular rib, the intermediate annular rib being provided at a part defined on a side of the retaining annular rib.

When the plunger is strongly drawn proximally to expand the retaining annular rib by the helical rib of the plunger, the deformation force applied proximally to the retaining annular rib is transmitted to the intermediate annular rib. The intermediate annular rib abuts on the inner peripheral surface of the barrel against the transmitted force, and inhibits deformation of the retaining annular rib. Therefore, expansion of the retaining annular rib beyond the predetermined extent is prevented. Accordingly, abutment between the proximal end surface of the helical rib and the distal end surface of the retaining annular rib is maintained, and the plunger proximally drawn is prevented from being separated. Further, the retaining annular rib is provided with the rib absent portion, so that the helical rib of the plunger can readily ride over the retaining annular rib. When the helical rib riding over the retaining annular rib is brought into strong contact with the retaining annular rib near the rib absent portion, and thereby resistance is generated, the intermediate annular rib is pressed from the inside and brought into strong contact with the barrel. Therefore, the rotational resistance of the gasket is also increased. Accordingly, the intermediate annular rib prevents turning of the gasket when the plunger is mounted, in particular, when the helical rib passes the rib absent portion.

Additional embodiments of the syringe may comprise the following.

(2) The syringe according to (1), in which the intermediate annular rib has an outer diameter configured to be smaller than the outer diameter of the distal side annular rib and the outer diameter of the proximal side annular rib.

(3) The syringe according to (2), in which the outer diameter of the intermediate annular rib is larger than the inner diameter of the barrel.

(4) The syringe according to (3), in which a contact area between the intermediate annular rib and an inner peripheral surface of the barrel is smaller than a contact area between the distal side annular rib and the inner peripheral surface of the barrel, and a contact area between the proximal side annular rib and the inner peripheral surface of the barrel.

(5) The syringe according to any of (1) to (4), in which the intermediate annular rib has a vertical cross-section comprising a top part and formed into a chevron shape.

(6) The syringe according to any of (1) to (5), in which the intermediate annular rib is provided to have an outermost projecting top part positioned at a side part on a proximal side of the retaining annular rib.

(7) The syringe according to any of (1) to (6), in which the helical projection has a distal end connected to a part adjacent to the rib absent portion of the retaining annular rib, and the helical projection has a surface on a distal side of a distal end part adjacent to a proximal end of the rib absent portion.

(8) The syringe according to any of (1) to (7), in which the head portion comprises a shaft portion, the helical rib is provided on the shaft portion, and the helical rib has a proximal end formed as a circumferentially extending portion extending in a circumferential direction of the shaft portion, substantially perpendicular to an axis of the shaft portion.

(9) The syringe according to any of (1) to (8), in which the syringe is a prefilled syringe.

The prefilled syringe according to an embodiment of the present invention comprises the following.

(10) A prefilled syringe comprising a syringe according to any of (1) to (9), a sealing member for sealing the distal opening portion of the barrel, and a medicine stored in the barrel.

What is claimed is:

1. A syringe comprising:
a cylindrically-shaped gasket comprising a closed distal end, an open proximal end, and an inner cavity portion extending distally from a proximal side;
a barrel comprising a distal opening portion, the barrel configured to slidably accommodate the gasket; and
a plunger comprising a head portion configured to be accommodated in the inner cavity portion of the gasket and a helical rib disposed on an outer surface of the head portion,
wherein the gasket comprises, on an inner surface of the inner cavity portion, a helical projection configured to threadedly engage with the helical rib of the plunger and a plunger retaining annular rib positioned on a distal side near the helical projection,
wherein the inner cavity portion further comprises an accommodation portion positioned distally from the plunger retaining annular rib, the accommodation portion configured to accommodate a part of the head portion of the plunger at which the helical rib is formed, and
wherein the gasket comprises, on an outer peripheral surface, a distal side annular rib having an outer diameter larger than an inner diameter of the barrel, a proximal side annular rib having an outer diameter larger than the inner diameter of the barrel, and an intermediate annular rib disposed between the distal side annular rib and the proximal side annular rib, wherein a portion of the intermediate annular rib is disposed opposite a portion of the plunger retaining annular rib, and
wherein an outer diameter of the intermediate annular rib smaller than the outer diameter of the distal side annular rib and the outer diameter of the proximal side annular rib,
wherein the plunger retaining annular rib has a rib absent portion for guiding, to the accommodation portion, the helical rib reaching the plunger retaining annular rib as threaded engagement is advanced between the plunger and the gasket, and the plunger retaining annular rib has one end and the other end formed by the rib absent portion, and the one end and the other end of the plunger retaining annular rib are located on the inner surface of the inner cavity portion at a location opposite the intermediate annular rib.

2. The syringe according to claim 1, wherein the outer diameter of the intermediate annular rib is larger than the inner diameter of the barrel.

3. The syringe according to claim 2, wherein a contact area between the intermediate annular rib and an inner peripheral surface of the barrel is smaller than a contact area between the distal side annular rib and the inner peripheral surface of the barrel and a contact area between the proximal side annular rib and the inner peripheral surface of the barrel.

4. The syringe according to claim 1, wherein the intermediate annular rib has a vertical cross-section comprising a top part and configured into a chevron shape.

5. The syringe according to claim 1, wherein the intermediate annular rib is configured to have an outermost projecting top part positioned at a side part on a proximal side of the plunger retaining annular rib.

6. The syringe according to claim 1, wherein the helical projection comprises a distal end connected to a part adjacent to the rib absent portion of the plunger retaining annular rib, and the helical projection comprises a surface on a distal side of a distal end part adjacent to a proximal end of the rib absent portion.

7. The syringe according to claim 1, wherein the head portion comprises a shaft portion, the helical rib is disposed on the shaft portion, and the helical rib comprises a proximal end formed as a circumferentially extending portion extending in a circumferential direction of the shaft portion substantially perpendicular to an axis of the shaft portion.

8. The syringe according to claim 1, wherein the syringe is a prefilled syringe.

9. A prefilled syringe comprising: the syringe according to claim 1; a sealing member for sealing the distal opening portion of the barrel; and a medicine stored in the barrel.

10. The syringe according to claim 1, wherein the intermediate annular rib extends in a direction perpendicular to the axis of the gasket.

11. The syringe according to claim 1, wherein an outermost projecting part of the intermediate annular rib is offset from an innermost projecting part of the plunger retaining annular rib in an axial direction of the gasket.

12. The syringe according to claim 1, wherein an outermost projecting part of the intermediate annular rib is disposed opposite a proximal portion of the plunger retaining annular rib.

13. The syringe according to claim 1, wherein a distal end surface of the intermediate annular rib is disposed proximal of a distal end surface of the plunger retaining annular rib.

14. The syringe according to claim 1, wherein a first portion of the intermediate annular rib is disposed opposite a proximal portion of the plunger retaining annular rib, and wherein a second portion of the intermediate annular rib is disposed opposite a distal end of the helical projection.

15. The syringe according to claim 14, wherein a distal end surface of the intermediate annular rib is disposed proximal of a distal end surface of the plunger retaining annular rib.

16. The syringe according to claim 1, wherein the intermediate annular rib inhibits deformation of the plunger retaining annular rib when the helical rib of the plunger rides over the plunger retaining annular rib.

* * * * *